United States Patent [19]
DiGuiseppi et al.

[11] Patent Number: 5,475,181
[45] Date of Patent: Dec. 12, 1995

[54] PROCESS FOR SELECTIVELY CONVERTING ETHENE TO ISOBUTYLENE OVER SELECTIVATED ZSM-35

[75] Inventors: Frank T. DiGuiseppi, Yardville; Scott Han, Lawrenceville; Roland H. Heck, Pennington, all of N.J.

[73] Assignee: Mobil Oil Corporation, Fairfax, Va.

[21] Appl. No.: 228,778

[22] Filed: Apr. 18, 1994

[51] Int. Cl.$^6$ ........................................... C07C 2/04
[52] U.S. Cl. ........................ 585/510; 585/520; 585/530
[58] Field of Search .................................. 585/510, 520, 585/533

[56] References Cited

U.S. PATENT DOCUMENTS

| | | |
|---|---|---|
| 3,960,978 | 1/1976 | Givens et al. . |
| 4,001,346 | 1/1977 | Chu . |
| 4,002,697 | 1/1977 | Chen . |
| 4,021,502 | 5/1977 | Plank et al. . |
| 4,100,215 | 7/1978 | Chen . |
| 4,101,595 | 7/1978 | Chen et al. . |
| 4,128,592 | 12/1978 | Kaeding . |
| 4,520,221 | 5/1985 | Hsia Chen ............................. 585/517 |
| 4,547,613 | 10/1985 | Garwood et al. ..................... 585/533 |
| 4,568,786 | 2/1986 | Hsia Chen et al. ................... 585/517 |
| 4,717,782 | 1/1988 | Garwood et al. ..................... 585/531 |
| 4,870,038 | 9/1989 | Page et al. ............................. 502/62 |
| 5,015,361 | 5/1991 | Anthes et al. ......................... 208/111 |
| 5,234,875 | 8/1993 | Han et al. .............................. 585/533 |
| 5,284,989 | 2/1994 | Apelian et al. ........................ 585/533 |

FOREIGN PATENT DOCUMENTS 8330139  9/1983  European Pat. Off. .

*Primary Examiner*—Anthony McFarlane
*Assistant Examiner*—E. D. Irzinski
*Attorney, Agent, or Firm*—Alexander J. McKillop; Dennis P. Santini; Laurence P. Hobbes

[57] ABSTRACT

The present invention relates to a process for the oligomerization of ethene to a product rich in isobutylene comprising contacting a feedstock comprising ethene under oligomerization conditions with a catalyst composition comprising a porous crystalline silicate having the structure of ZSM-35 zeolite whose surface has been at least partially deactivated for acid catalyzed reactions by a) coking or b) chemisorption of a surface-deactivating agent, e.g., collidine, which possesses an average cross section diameter greater than that of the zeolite pores.

11 Claims, No Drawings

PROCESS FOR SELECTIVELY CONVERTING ETHENE TO ISOBUTYLENE OVER SELECTIVATED ZSM-35

BACKGROUND OF THE INVENTION

This invention relates to a process for the catalytic conversion of ethene to provide an oligomer product which is rich in C4's, especially, isobutylene.

The process employs a selectivated ZSM-35, which exhibits unique characteristics under the process conditions described below.

Ethene is a by-product of petroleum refining and is, as well, a commodity petrochemical. Today much of the ethene generated during refining and some of the lower concentration ethene streams from petrochemical production are burned as fuel. Significant economic value could be derived if these ethene-containing streams could be processed to generate higher boiling, more valuable hydrocarbons from the ethene. Interest in making C4 olefins from ethene has increased in recent years as a way of utilizing ethene and also as a way to make 2-butene for alkylation purposes. In addition, since isomerization within the C4 olefin group is well-known, linear C4 olefin can be used to make isobutylene, an intermediate for t-butyl methyl ether (MTBE).

Conversion of olefins to gasoline and/or distillate products is disclosed in U.S. Pat. Nos. 3,960,978 and 4,021,502 (Givens, Plank and Rosinski) wherein gaseous olefins in the range of ethene to pentene, either alone or in admixture with paraffins are converted into an olefinic gasoline blending stock by contacting the olefins with a catalyst bed made up of a ZSM-5 type zeolite. Such a technique has been developed by Garwood, et al, as disclosed in European Patent Application No. 83301391.5, published Sep. 29, 1983.

The prior art teaches conversion of $C_2+$ monoalkenes to an equilibrium olefin mixture under conditions which maximize the formation of higher olefins. For example, zeolites such as ZSM-5 are known to convert lower olefins to higher olefins. Conversion of lower olefins, especially propene and butenes, over HZSM-5 is effective at moderately elevated temperatures and pressures. Lower olefinic feedstocks containing $C_2-C_6$ alkenes may be converted selectively; however low severity conditions do not convert a major fraction of ethene. While propene, butene-1, and others may be converted to the extent of 50% to 95% at temperatures up to 400° C. and moderate pressures from ambient to 5500 kPa, only about 10% to 30% of the ethene component will be converted using HZSM-5 or similar acid zeolites, according to U.S. Pat. No. 4,717,782 to Garwood et al. The olefin interconversion process must cope with undesirable side reactions which yield aromatics and paraffins, the presence of which is acutely noticed at the relatively high temperatures (>700° F.) at which ethene conversion and formation of $i-C_4^=$ and $i-C_5^=$ formation is thermodynamically favored. In order to avoid such undesirable side reactions, the '782 Garwood et al reference teaches the use of a bifunctional nickel-zeolite catalyst for oligomerizing ethene streams containing hydrogen and hydrogen sulfide at 100° to 450° C. and 200–3600 kPa (15–500 psig), wherein water is fed with the feedstock to prevent reduction of the nickel component.

Isobutylene is desirable inasmuch as it can be etherified with lower $C_1-C_5$ aliphatic alcohols, to produce alkyl tertiary butyl ethers. The ethene conversion product comprising a high proportion of $C_4$ olefins can be blended directly into "base" gasoline, or, to etherify all, or a portion of the product with lower $C_1-C_5$ aliphatic alcohols. The latter option is especially advantageous because the etherification reaction proceeds apace and with gratifying selectivity.

Thus, it is of interest to find catalysts of increased activity which are able to convert ethene more selectively into butenes at higher feed rates, lower reaction pressures or with more dilute ethene streams and simultaneously minimize production of the higher oligomers. Moreover, given the increased demand for alkyl tert butyl ethers such as MTBE, it would be highly desirable to provide a process which produces not only linear butenes from olefins, but isobutylene as well.

It is known in the art that surface acidity of zeolitic catalysts can be modified by treatment with various reagents. U.S. Pat. No. 4,870,038 to Page et al discloses a process for producing substantially linear hydrocarbons by oligomerizing a lower olefin at elevated temperature and pressure with siliceous acidic ZSM-23 whose surface is rendered substantially inactive for acidic reactions, e.g., by contact with 2,4,6-collidine (2,4,6-trimethylpyridine, gamma-collidine). U.S. Pat. No. 5,015,361 to Anthes et al discloses a method for catalytic dewaxing which employs surface acidity deactivated zeolite catalysts. The reduction in surface acidity serves to reduce the amount of lower value cracked products obtained during dewaxing. U.S. Pat. No. 4,101,595 teaches the modification of zeolites by exchange and similar technology with large cations such as $N^+$ and $P_+$ and large branched compounds such as polyamines and the like. Bulky phenolic and silicating zeolite surface-modifying agents are described in U.S. Pat. Nos. 4,100,215 and 4,002,697, respectively. As disclosed in U.S. Pat. Nos. 4,520,221 and 4,568,786, zeolites which have been surface-deactivated by treatment with bulky dialkylamines are useful as catalysts for the oligomerization of lower olefins such as propylene to provide lubricating oil stocks.

Deposition of carbonaceous materials by coke formation can also shift the effective ratio of intra-crystalline acid sites to surface active sites, as disclosed in U.S. Pat. No. 4,547,613, wherein a zeolite catalyst is conditioned by contact with $C_{2-16}$ olefin at 400° to 1000° F. at 0 to 100 psig for 1–70 hours. The conditioned catalyst provides an oligomerized olefin product having a high viscosity index. U.S. Pat. No. 5,234,875 to Han et al. teaches coke-selectivating zeolites under high pressure coking conditions for use in oligomerization of lower olefins. Other examples of coke-selectivation of zeolite catalysts are set out in U.S. Pat. Nos. 4,001,346 to Chu et al. and 4,128,592 to Kaeding et al. All of the foregoing references are incorporated herein by reference.

SUMMARY OF THE INVENTION

The present invention relates to a process for the oligomerization of ethene to a product rich in butenes and low in C5+ compounds comprising contacting a feedstock comprising ethene under oligomerization conditions with a catalyst composition comprising a porous crystalline silicate having the structure of ZSM-35. The ZSM-35, prior to its use in oligomerization is selectivated by selective coking or poisoning with contacted under non-aqueous conditions with an organic nickel compound having an effective diameter less than about 5.4 Å and then calcined under oxidizing conditions to provide a NiO ZSM-35 catalyst. The catalyst composition thus prepared exhibits reduced aging during oligomerization as well as enhanced $C_4$ olefins selectivity, enhanced isobutylene/linear butene molar ratios selectivity and enhanced ethene conversion capability.

DETAILED DESCRIPTION OF PREFERRED EMBODIMENTS

Feed

The ethene feed to the oligomerization reaction of the present invention can be a purified ethene stream or more commonly an impure ethene stream diluted with other hydrocarbons and other gases such as $N_2$, $H_2$, etc. Such diluent hydrocarbons can be, saturated hydrocarbons, such as ethane, propane, butane and the like and, unsaturated hydrocarbons, such as propene, butenes, pentenes and the like. The exact composition of the feed stream will depend upon its source. In one embodiment, the feedstock comprises unsaturated gas plant treated deethanizer overhead.

Catalyst

The catalyst composition of the present invention comprises a ZSM-35 crystalline silicate molecular sieve, optionally composited in an inorganic oxide matrix. ZSM-35 has channels described by 10-membered rings of T (=Si or Al) or oxygen atoms, i.e., it is an intermediate pore zeolite, distinct from small pore 8-ring or large pore 12-ring zeolites. It differs, however, from other intermediate pore 10-ring zeolites, such as ZSM-5, ZSM-11, ZSM-57 or stilbite, in having a smaller 10-ring channel.

ZSM-35 is more particularly described in U.S. Pat. No. 4,016,245, the entire contents of which are incorporated herein by reference. For purposes of the present invention, ZSM-35 is considered to include its isotypes, e.g., ferrierite, FU-9, ISI-6, NU-23, and Sr-D. An example of a piperidine-derived ferrierite is more particularly described in U.S. Pat. No. 4,343,692, the entire contents of which are incorporated herein by reference. Other synthetic ferrierite preparations are described in U.S. Pat. Nos. 3,933,974; 3,966,883; 4,000,248; 4,017,590; and 4,251,499, the entire contents of all being incorporated herein by reference. Further descriptions of ferrierite are found in Bibby et al, "Composition and Catalytic Properties of Synthetic Ferrierite," Journal of Catalysis, 35, pages 256–272 (1974).

When the zeolites are prepared in the presence of organic cations, they may be quite inactive possibly because the intracrystalline free space is occupied by the organic cations from the forming solution. The zeolite may be activated by heating in an inert or oxidative atmosphere to remove the organic cations, e.g. by heating at over 500° C. for 1 hour or more. The hydrogen form can then be obtained by base exchange with ammonium salts followed by calcination, e.g., at 500° C. in air. Acid treatment may result in dealumination and is therefore not typically practiced. Other cations, e.g. metal cations, can be introduced by conventional base exchange or impregnation techniques.

The zeolite may be incorporated in another material usually referred to as a matrix or binder. Such matrix materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be composited with the zeolite include those of the montmorillonite and kaolin families, which families include the subbentonites and the kaolins commonly known as Dixie, McNamee, Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the zeolites employed herein may be composited with a porous matrix material, such as silica, alumina, zirconia, titania, silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia. The matrix can be in the form of a cogel. A mixture of these components could also be used.

Of all the foregoing materials, silica may be preferred as the matrix material owing to its relative inertness for catalytic cracking reactions which are preferably minimized in the instant processes. The relative proportions of finely divided zeolite and inorganic oxide gel matrix vary widely with the zeolite content ranging from about 1 to about 90 percent by weight and more usually in the range of about 30 to about 80 percent by weight of the composite. In other words, the catalyst composition can comprise 10 to 99 wt % of a refractory inorganic oxide binder, preferably 20 to 70 wt % of a silica binder.

Selectivation

The extent to which the zeolite can be surface-deactivated can vary over considerable limits, depending on the conditions of the deactivation procedure, and still provide significant improvement over the same zeolite which has not been surface-deactivated. In general, a reduction in surface acid sites on the order of at least about 10%, and preferably at least about 20%, can be readily achieved employing the methods described below.

Deactivation of the surface acid catalytic activity of the selected zeolite can be accomplished in accordance with known and conventional methods. Thus, treatment of the zeolite surface with bulky basic compounds such as amines, phosphines, phenols, polynuclear hydrocarbons, cationic dyes, and the like, will provide the requisite reduction in surface acid catalytic activity.

These surface deactivating agents should have an average cross section diameter of about 5 Angstroms or greater in order to prevent their being sorbed within the zeolite. Examples of suitable amines include monoamines, diamines, triamines, aliphatic and aromatic cyclic amines and heterocyclic amines, porphines, phthalocyanines, 1,10-phenanthroline, 4,7-diphenyl-1,10-phenanthroline, 3,4,7,8-tetramethyl-1,10-phenanthroline, 5,6-benzoquinoline, 2,2':6',2"-terpyridine, 2,4,6-tris(2-pyridyl)-S-triazine and 2,3-cyclododecenopyridine. Examples of phosphines include triphenylphospine and 1,2-bis(diphenylphosphine)ethane. Suitable phenols are, for example, di-t-butylphenol, alkylated naphthol and 2,4,6-trimethylphenol. Polynuclear hydrocarbons include substances such as pyrene and phenanthrene. Cationic dyes include thionine, methylene blue and triphenylmethane dyes, such as malachite green and crystal violet. Another surface modification technique is deactivation by treating with metal compounds. Suitable metal compounds are magnesium acetate, metalporphines such as hemin or iron (III) porphine chloride, cobalticinium chloride $(C_5H_5)_2COCl$ and titanocene dichloride (biscyclopentadienyl titanium dichloride) and large complex cations such as $[Co(NH_2R)_6]^{2+}$ where R is H or alkyl, $[Pt(NH2R)_4]_{2+}$ where R is alkyl, $[Co(en)_3]^{3+}$ where en is ethylenediamine and manganese (III) meso-tetraphenylporphine.

The zeolites can also be treated with organic silicon compounds as described in U.S. Pat. Nos. 4,100,215 and 4,002,697, the contents of which are incorporated by reference herein, to impart the desired degree of surface deactivation while being essentially free of carbonaceous deposits. Such treatment involves contacting the catalyst with a silane surface-modifying agent capable of deactivating catalytic (acidic) sites located on the external surface of the zeolite by chemisorption.

Amines having an average cross section diameter larger than about 5 Angstroms are especially suitable for reducing zeolite surface acid catalysis activity. Examples of such amines include substituted quinolines, heterocyclic amines and alkyl-substituted pyridines such as 2,4- or 1,6-dialkyl pyridines and 2,4,6-trialkyl pyridines. Preferred are bulky, sterically-hindered di-ortho-alkyl pyridines such as 2,6-di-tert-butylpyridine as described in U.S. Pat. Nos. 4,520,221 and 4,568,786 referred to above, and 2,4,6-collidine (2,4,6-trimethyl pyridine, gamma-collidine) as disclosed in U.S. Pat. No. 4,870,038, the contents of which are incorporated herein by reference.

The zeolites used in the present invention can be contacted with the surface deactivating agent by adding small amounts of said agent to the feedstock which is to be subjected to double bond isomerization conditions. Suitable amounts of surface deactivating agent in the feed can range from 0.01 to 10 wt %, preferably 0.5 to 5 wt %, say, 1 to 3 wt % of the feedstock. This concentration of deactivating agent in the feed is maintained until the cumulative moles of amine fed per mole of acid ($H^+$) in the zeolite reaches 0.2 to 0.5. Thereafter the concentration of deactivating agent in the feed is decreased to a maintenance level of 10 to 1000 ppm. The required maintenance level concentration will vary with the amine used and the conditions employed. This level can be adjusted to maintain the desired level of oligomers in the reactor product.

Alternatively, the zeolite can be treated with the agent prior to contact with the organic feedstock. Such treatment can be accomplished by contacting the zeolite with 0.0001 to 1.0 parts by weight, preferably 0.0005 to 0.5 parts by weight, say 0.001 to 0.05 parts by weight of the surface deactivating agent, per weight of zeolite, preferably dissolved in a solvent, e.g. pentane.

The ZSM-35 zeolite used in the present invention can be coke-selectivated by contacting the above-described zeolite, preferably composited with a porous matrix material, e.g., alumina, with a thermally decomposable organic compound, e.g., ethylene, at a temperature in excess of the decomposition temperature of said compound and at a pressure of at least 400 psig, e.g., 400 to 1100 psig, preferably 500 to 900 psig, e.g., 750 to 850 psig. The catalyst is usually exposed to the above coking conditions for a period of 0.1 to 14 days, preferably 12 to 48 hours prior to its use in organic compound conversion. The coking temperatures can range from 200 to 500° C., preferably 250° to 400° C., say 325° to 375° C. Generally, higher coking temperatures within these ranges are preferred, along with lower olefins as the source of coke which require higher coking temperatures, e.g. ethylene or propylene, in order to lay down a harder coke. Such high pressure coking conditions are set out in further detail in U.S. Pat. No. 5,234,875, which is incorporated herein by reference.

Optionally, the zeolite can be subjected to thermal treatment prior to coking, including steaming or calcination in air, hydrogen or an inert gas, e.g., nitrogen or helium.

An especially useful modifying treatment entails steaming of the zeolite by contact with an atmosphere containing from about 5 to 100 percent steam at a temperature of from about 250° to 1000° C.

Organic materials, thermally decomposable under the above temperature conditions to provide coke depositions, encompass a wide variety of compounds including by way of example, hydrocarbons, such as paraffinic, cycloparaffinic, cycloolefinic and aromatic; oxygen-containing organic compounds such as alcohols, aldehydes, ethers, ketones and phenols; and heterocyclics such as furans, thiophenes, pyrroles and pyridines. Usually, it is contemplated that a thermally decomposable hydrocarbon, such as a lower olefin, e.g. $C_2$ to $C_6$, alone or admixed with a lower paraffinic hydrocarbon, e.g., $C_2$ to $C_6$, will be the source of coke. Ethylene or propylene is particularly desirable. Lower olefins are preferable to higher olefins as a source of coke inasmuch as they require higher temperatures to produce coking and thus render a harder, more durable coke on the catalyst surface. The thermally decomposable organic material may also be combined with 1 to 90 mol % of an inert gaseous material, e.g., nitrogen or helium. A particularly suitable feed comprises a mixture of 30 mol % organic, e.g., ethylene and 70 mol % inert diluent, e.g., nitrogen.

In one embodiment of the invention, the coke is baked after being laid down on the zeolite to further enhance the stability and durability of the coked catalyst. This can be achieved by ceasing or limiting the flow of the decomposable organic compound over the zeolite while maintaining the catalyst at the temperatures employed during the coking process for a period of time sufficient to provide a harder coke, e.g., 1 to 96 hours, preferably 12 to 48 hours.

The regeneration of spent zeolite catalyst used in the oligomerization reaction is carried out oxidatively or hydrogenatively employing procedures known in the art.

Oligomerization Conditions

The oligomerization process of the present invention can be carried out by contacting the feedstock with the catalyst composition under conditions comprising temperatures ranging from 150° C. to 400° C., preferably from 250° C. to 370° C., pressures ranging from 2 to 15 atm, preferably pressures ranging from 5 to 8 atm, WHSV ranging from 0.1 to 5, preferably WHSV ranging from 0.5 to 2.0, and wherein at least 10% by weight of said ethene, preferably at least 20% by weight of said ethene is converted with an overall $C_4$ olefins selectivity of at least 30 wt %, preferably at least 40 wt % based on product stream and an isobutylene to linear butenes molar ratio of at least 0.3, preferably at least 0.4, in the product.

The reaction is desirably carried out in a fixed bed reactor although an ebullated, slurry or fluidized bed or other type of reactor can be useful.

The following examples provide specific illustrations for the present invention.

EXAMPLE 1

Preparation of ZSM-35

ZSM-35 was prepared according to the following mole ratios: $SiO_2/Al_2O_3=21.5$, $OH^-/SiO_2=0.11$, $H_2O/SiO_2=13.2$, $N/Al_2O_3=6.5$, $OH^-/H_2O=0.008$ The reagents used were 50% NaOH, $Al_2(SO_4)_3 \cdot 18H_2O$, HiSil$^R$ silica available from PPG Industries, Chemical Division (USA), and pyrrolidine. After measuring out appropriate quantities, the reagents were introduced in the following order: $H_2O$, NaOH, aluminum sulfate, silica, and pyrrolidine. 0.2 wt. % ZSM-35 was added as seed crystals. The reaction mixture was heated to 100° C. and held at temperature with agitation for 106 hrs. The product was cooled, filtered, and washed with water. Conversion to the acid form involved calcination in air at 538° C., ammonium exchange using aqueous ammonium nitrate, washing with water, and nitrogen calcination at 538° C.

EXAMPLE 2

Preparation of Collidine-Selectivated ZSM-35

The catalyst from Example 1 was selectivated with 2,4, 6-collidine in the following manner. 1 part of 2,4,6-collidine was dissolved in a minimum amount of pentane required to wet the catalyst and added to 99 parts of the base catalyst from Example 1. The mixture was stirred and the pentane allowed to evaporate. The finished catalyst was used without further treatment.

EXAMPLE 3

Preparation of Coke-Selectivated ZSM-35

The catalyst of Example 1 was precoked with a flowing stream of nitrogen/ethylene at 800 psig and 350° C. for 30 hours. After coking the catalyst the catalyst was held at temperature for 26 hours before it was cooled and restreamed with the nitrogen/ethylene feed.

EXAMPLE 4

Oligomerization of Dilute Ethene Stream

The catalysts of Examples 1, 2 and 3 were used in the olefin oligomerization of a dilute 65/35 (wt) stream of nitrogen/ethene at 100 psig under the conditions set out in the Table below. The catalysts of Example 2 and Example 3 gave products containing significantly greater amounts of isobutylene than the non-selectivated catalyst of Example 1 (22 wt % versus 13 wt %). Moreover, the selectivated catalysts provided reduced amounts of C6+ hydrocarbons than the non-selectivated catalyst (50 to 60 wt % versus 74 to 81 wt %).

3. The process of claim 1 wherein said coking is carried out in the presence of an olefin selected from the group consisting of ethene and propene, at pressures ranging from 500 to 900 psig, for a period of time ranging from 0.1 to 14 days.

4. The process of claim 1 wherein said surface-deactivating agent is selected from the group consisting of amines, phosphines, phenols, polynuclear hydrocarbons, cationic dyes and organic silicon compounds.

5. The process of claim 4 wherein said surface-deactivating agent is selected from the group consisting of monoamines, diamines, triamines, aliphatic cyclic amines, aromatic cyclic amines, porphines, phthalocyanines, 1,10-phenanthroline, 4,7-diphenyl-1,10-phenanthroline, 3,4,7,8-tetramethyl-1,10-phenanthroline, 5,6-benzoquinoline, 2,2',6',2"-terpyridine, 2,4,6-tris(2-pyridyl)-S-triazine and 2,3-cyclododecenopyridine.

6. The process of claim 4 wherein said surface-deactivating agent is selected from the group consisting of substituted quinolines, heterocyclic amines, and alkyl-substituted pyridines.

7. The process of claim 1 wherein said surface-deactivating agent is 2,4,6-collidine.

8. The process of claim 1 which further comprises adding said surface-deactivating agent to said feedstock.

9. The process of claim 1 which further comprises contacting said ZSM-35 with 0.0001 to 1.0 parts by weight of

TABLE

| Catalyst Pretreatment | COLLIDINE (Ex. 2) | | | NONE (Ex. 1) | | | COKE SELECTIVATED (Ex. 3) | | |
|---|---|---|---|---|---|---|---|---|---|
| Temp. °C. | 250 | 300 | 325 | 230 | 250 | 265 | 310 | 340 | 370 |
| WHSV | 0.5 | 0.5 | 1.0 | 0.5 | 0.5 | 0.5 | 0.5 | 0.5 | 0.5 |
| Ethylene Conversion | 0 | 31 | 30 | 7 | 14 | 31 | 17 | 23 | 22 |
| Product Distribution, Wt. % | | | | | | | | | |
| $C_3$'s | 0 | 3.0 | 2.3 | 0 | 0 | 0.3 | 2.2 | 2.8 | 3.4 |
| Isobutene | 0 | 22.0 | 18.1 | 8.1 | 13.0 | 9.5 | 19.6 | 19.8 | 23.1 |
| n-Butene | 0 | 22.8 | 17.8 | 14.9 | 13.0 | 8.2 | 21.1 | 20.3 | 25.5 |
| Isobutane | 0 | 0.0 | 0.0 | 0.0 | 0.0 | 0.0 | 0.7 | 0.0 | 0.0 |
| N-Butane | 0 | 1.1 | 0.5 | 0.0 | 0.0 | 0.0 | 0.3 | 0.0 | 0.0 |
| $C_6+$ | 0 | 51.1 | 61.3 | 77.0 | 74.0 | 81.0 | 57.1 | 57.1 | 48.0 |
| Total | 0 | 100.0 | 100.0 | 100.0 | 100.0 | 100.0 | 100.0 | 100.0 | 100.0 |

Having thus clearly and objectively stated the problem to be solved, and its solution by the invention disclosed herein, and having provided a detailed description and illustrations of the best mode of practicing the invention, it is to be understood that no undue restrictions are to be imposed by reason thereof, and particularly, that the invention is not restricted to a slavish adherence to the details set forth herein.

What is claimed is:

1. A process for the oligomerization of ethene to isobutylene comprising contacting a feedstock comprising ethene under oligomerization conditions with a catalyst composition comprising a ZSM-35 zeolite whose surface has been at least partially deactivated for acid catalyzed reactions by a) coking or b) chemisorption of a surface-deactivating agent which possesses an average cross section diameter greater than that of the zeolite pores.

2. The process of claim 1 wherein said coking is carried out in the presence of olefin at pressures of at least 400 psig.

said surface-deactivating agent per weight of said zeolite.

10. The process of claim 1 wherein said feedstock contains ethene, said ethene comprises greater than 50 wt % of total olefin content of said feedstock, said oligomerization conditions comprise a temperature which ranges from 150° C. to 400° C., a pressure which ranges from 2 to 15 atm, and a weight hourly space velocity which ranges from 0.1 to 5, and wherein at least 10% by weight of said ethene is converted with an overall $C_4$ olefins selectivity of at least 30 wt % based on total olefins and an isobutylene to linear butenes molar ratio of at least 0.3.

11. The process of claim 10 wherein said temperature ranges from 250° C. to 370° C., said pressure ranges from 5 to 8 atm, said weight hourly space velocity ranges from 0.5 to 2.0, and wherein at least 20% by weight of said ethene is converted with an overall $C_4$ olefins selectivity of at least 40 wt % based on total olefins in said feedstock and an isobutylene to linear butenes molar ratio of at least 0.4.

* * * * *